United States Patent [19]

Friel, Jr. et al.

[11] Patent Number: 4,960,540

[45] Date of Patent: Oct. 2, 1990

[54] ALKOXYLATED BIS-AMIDE DEFOAMING COMPOUNDS

[76] Inventors: Thomas C. Friel, Jr., 3 Bitterroot La., Savannah, Ga.; Anthony J. O'lenick, Jr., 4437 Park Dr., Suite E, Norcross, Ga. 30093

[21] Appl. No.: 397,998

[22] Filed: Aug. 24, 1989

[51] Int. Cl.$^5$ .................. C07C 233/01; B01D 19/04; D21C 3/28

[52] U.S. Cl. .................. 252/358; 252/321; 564/159; 162/5; 162/72

[58] Field of Search .......... 564/159; 252/321, 358; 162/5, 72, 76

[56] References Cited

U.S. PATENT DOCUMENTS

| | | | |
|---|---|---|---|
| 3,180,786 | 4/1965 | Domba et al. | 252/321 |
| 3,730,907 | 5/1973 | Shane et al. | 252/321 |
| 3,751,370 | 8/1973 | Stimberg et al. | 252/358 |
| 3,923,683 | 12/1975 | Michalski et al. | 252/321 |
| 4,107,073 | 8/1978 | Maciaszek | 252/321 |
| 4,556,497 | 12/1985 | Horodysky | 564/159 |
| 4,696,761 | 9/1987 | Haubennestel et al. | 252/358 |

*Primary Examiner*—David L. Lacey
*Assistant Examiner*—Todd J. Burns

[57] ABSTRACT

The present invention involves new anti-foam compositions which control foaming in aqueous systems and by nature of their inverse cloud point characterisitics are insoluble and particulate above their inverse cloud point, and soluble below it. This property makes them particulate non-depositing defoamers. As the defoamed aqueous system cools down these novel products become soluble, preventing insoluble material (pitch) from depositing on process equipment and matter being processed. The anitfoam composition is an alkoxylated bis-amide of the following formula:

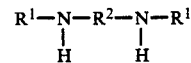

where
$R^1$ is

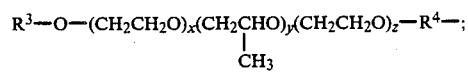

$R^2$ is $-(CH_2)_a-$;
$R^3$ is alkyl $C_{12}$ to $C_{20}$;

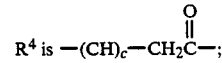

x,y,z are each independently integers from 0 to 20;
a is an integer from 1 to 5;
c is an integer from 0 to 5;
$R^5$ is selected from H, $CH_3$, $C_2H_5$, $C_3H_6$.

13 Claims, No Drawings

ALKOXYLATED BIS-AMIDE DEFOAMING COMPOUNDS

BACKGROUND

Many industrial processes utilize aqueous solutions and suspensions in which foam production is detrimental to the efficient conduct of the process. Traditional defoaming agents which are commonly employed control foam during these processes but may lead to insoluble material deposition upon process equipment, requiring costly and inconvenient clean up and down time. Examples of processing in which foam is detrimental, and insoluble material deposition is commonly found includes, but is not limited to, paper manufacturing, paper de-inking, textile processing and sewage disposal systems. The insoluble material used for de-foaming may actually deposit upon the surface of the substrate being processed. If this occurs, the substrate will be of inferior quality and may have to be reprocessed to remove insoluble material.

In the paper industry the kraft process is one of the most frequently used alkaline pulping processes. It is valuable in that spent chemicals may be recycled and reused thus decreasing processing costs. A large disadvantage of this process is the occurrence of foam during the pulp screening and washing procedures.

The kraft process as taught in U.S. Pat. No. 3,215,635 to Liebling is generally described as being performed by first cooking the wood chips in digesters and then drawing off the spent chemicals for reuse. The resulting pulp fibers are then washed free in brown stock washers of a large amount of residual chemicals. These washers are a series of vats usually three or four in number which alternatively dilute the pulp with water and thicken it by picking it up on large rotary screens. From the brown stock washers, the pulp travels to the screen room where it is again diluted with water and put through vibrating screens which accept the now completely delignified fibers and reject the clumps of unpulped fibers, knots and other foreign material. Foam problems are severe in the screen room since the diluted pulp is subjected to violent agitation by the screens. The water removed from the pulp after the screening operations is referred to as the dilute black liquor and, for the sake of economy, is normally used as the dilution water for the third and fourth stage of the brown stock washers. The dilute black liquor is a foaming material, containing from about 0.001% to 0.1% by weight of solids and has a pH of about 12. The foaming of the dilute black liquor increases with the increase of the resin content of the wood used in this process.

Defoamers are generally used in most alkaline pulp mills during the screening operations so that a more efficient screening is accomplished and to prevent the pulp thickeners, utilized after the screening operations, from becoming clogged with entrapped air. When water dispersible defoamers are used during the screening operation, the control of foam and entained air in the screening operation contributes to the washing efficiency of the pulp during the alkaline pulping process. This is accomplished by the fact that the screening efficiency of the pulp is increased, allowing ease of flow of the pulp throughout the thickeners and subsequent washers.

Additionally the paper de-inking process uses detergents which can cause considerable undesired foam when performing the desired removal of ink. More detailed descriptions of such processes are found in standard textbooks, such as A. M. Schwartz and J. W. Perry "Surface Active Agents", Vol. I (1949); and "Surface Active Agents and Detergents" Vol. II (1958). Interscience Publishers, N.Y., the descriptions of which are incorporated herein by reference.

The de-inking agents are used in solution in substantially aqueous media. The temperature of the de-inking solution may vary anywhere from room temperature, e.g., 40°–70° F. (4°–20° C.), up to about 200° F. (95° C.). Best results are achieved with the de-inking solutions described herein when they are alkaline in pH. It therefore is desirable that an alkali be included therein. Although any suitable alkali or alkaline earth metal hydroxide or salt may be employed, the alkali metal hydroxides and salts, such as sodium hydroxide, potassium hydroxide, soda ash and the like are preferred. Enough of the alkali should be added to maintain the pH of the de-inking solution between about 7.0 and 11.5, or even higher, and preferably at least 7.1.

In preparing the de-inking solution, water is charged to the reactor or pulper and about 0.3 to 3 percent, based on the weight of the paper, of the de-inking agent described hereinabove is added. The de-inking agent is preferably added to the water prior to the addition of the wastepaper or waste.

To the resulting solution is added the printed paper, scrap or waste. The printed cellulosic charge may, if desired, be shredded by appropriate means prior to treatment. This, however, is not necessary, and the waste material may be added to the treating solution without shreddeding or without any subdivision in size whatsoever. It is one of the advantages of this invention that costly shredding or pulping techniques prior to de-inking need not be employed. Thus, the waste material to be de-inked is preferably added to the testing solution in its naturally dry condition, e.g., without being subjected to moisture or water other than that which is normally present in the atmosphere. Although de-inking will occur if the waste material is first slurred or pulped in water, in general it has been found that the results achieved are inferior to those obtained when the waste material is added to the treating solution in its naturally dry condition, i.e., in equilibrium with its natural atmospheric environment. Although not wanting to be restricted to this interpretation, it appears that wetting the waste material with water prior to subjecting it to the chemical treatment described herein has a tendency to set the ink and make it more difficult to remove from the cellulosic fibers. The amount of the scrap or waste added to the treating solution should be controlled. In general, the percent of cellulosic by weight of the aqueous de-inking solution should be below 10 percent and preferably below 6.0 percent, or between about 4.0 and 6.0 percent. Good results are obtained when the de-inking solution contains about 5 to 5.5 percent lb. weight of paper and this value appears to be optimum. The scrap is retained in the treating solution until substantial defiberization and separation of the ink takes place.

Following treatment, the defibered material is dropped to a chest or other reservoir, after which it is diluted with water to a solids content of between about 0.5 and 1.5 percent, preferably about 1.0 percent, based upon the solution weight. Next, the pump is separated from the solution and washed and thickened by well know methods. Optionally, the pulp is then acidified to a pH of between about 4 and 6.5, preferable between about 4.5 to 5.5, thickened and then formed into a web.

In the de-inking process undesirable foam is encountered most commonly when high temperature and high agitation are experienced. It is also at this time that maximum detergency is needed to remove ink form the paper. Standard defoamers based upon ethylene bis-stearamide, silicone oils, or mineral oils while effective at the high temperatures and agitation conditions, become insoluble at lower temperatures and deposit on process equipment causing what is commonly referred to as pitch. Products of this invention have the defoaming properties of ethylene bis-stearamide, silicone oils, or mineral oils, but become soluble below their inverse cloud point.

BACKGROUND OF THE INVENTION

There are several references to foam control agents in the literature. Most use (1) water insoluble components like mineral oil, ethylene bis-stearamide, etc., or (2) emulsifier like soaps, ethoxylated esters, polyethylene glycols esters, etc. There are numerous formulations in the literature, U.S. Pat. No. 3,180,836 by Myron Jursich claims that alkoxylated castor oil can be used as an emulsifier in foam control formulations. The material functions like standard nonionics in the degree of defoaming. Many standard formulations used as defoamers have water insoluble oils and other components which are emulsified by use of surface active agents.

Invention

The invention relates to a novel bis amide product which conforms to the following structure;

$$R^1-N-R^2-N-R^1$$
$$\;\;\;\;\;|\;\;\;\;\;\;\;\;\;|$$
$$\;\;\;\;\;H\;\;\;\;\;\;\;H$$

wherein;
$R^1$ is $$R^3-O-(CH_2CH_2O)_x(CH_2CHO)_y(CH_2CH_2O)_z-R^4-$$
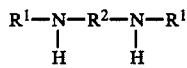

$R^2$ is $-(CH_2)_a-$
$R^3$ is alkyl having from 12 to 20 carbon atoms;

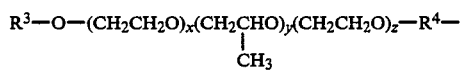

$R^4$ is $-(CH)_c-CH_2C-$ ;

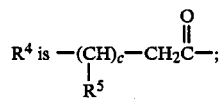

x,y,z are each independently integers from 0 to 20;
a is an integer from 1 to 5;
c is an integer from 0 to 5;
$R^5$ is selected from H, $CH_3$, $C_2H_5$, $C_3H_6$.

Another aspect of the present invention is the application of alkoxylated bis-amide which becomes completely insoluble and particulate above its inverse cloud point. This insolubility gives the molecule its superior defoaming properties. Selection of a custom tailored molecule for a given process temperature allows for application of these compounds over a wide operating temperature range, making these compounds applicable to many different industrial processes.

The compounds cited in the referenced patents defoam because an insoluble oil phase disrupts the foam at the foam/air/ water interface by replacement with an air/oil/ water interface.

The problem with the emulsified oil systems is that there are three essential parts of the formulation;
1 Water
2 An insoluble oil in wax present to defoam
3 An emulsifier or dispersant present to disperse the insoluble oil in wax During the process the formulation is added to initiate anti-foam action in the aqueous solution usually at elevated temperatures, then in a subsequent step the water is removed from the product being processed, i.e., fiber, textile material, sewage, etc. With removal of water the emulsion breaks and the insoluble materials rain out causing "pitch". Pitch is the insoluble ax or oil that deposits on the equipment after the defoamer has worked and the water has been removed.

Considerable down time and increased expense are involved to clean up equipment. It is the object of this invention to provide "defoaming" materials which can be used alone or in non depositing combination with other ingredients to defoam aqueous processes which are run at slightly elevated temperatures.

Compounds of the present invention have been found to defoam above their inverse cloud point by virtue of their insolubility and then become soluble upon cooling (Below their inverse cloud point).

The inverse cloud point phenomena which occurs as one heats an aqueous solution to a critical temperature has been well documented. More detailed descriptions of this are found in standard textbooks, such as A. M. Schwartz and J. W. Perry "Surface Active Agents", Vol. I (1949); and "Surface Active Agents and Detergents", Vol. II (1958). Interscience Publishers, N.Y., the descriptions of which are incorporated herein by reference. Standard nonionics which exhibit this inverse cloud point phenomena do not exhibit defoaming properties, and consequently are not effective in defoaming processes.

This invention teaches that alkoxylated alcohols are reacted with a suitable "acid source" to give an intermediate ether carboxylic acid alkoxylate which is subsequently reacted with polyamines like ethylene diamine to give materials which defoam by virtue of their particulate nature above their inverse cloud point yet are soluble below it. The inverse cloud point is defined as that temperature at which the test material becomes insoluble in water as evidenced by a haze or insoluble material in the liquor.

The following explanations are appropriate to the understanding the invention. One gram of each of the test antifoam materials was added to 100 grams of distilled water. The % transmission was recorded as the temperature was raised. Since ethylene-bis-stearamide is insoluble in water at all temperatures, it floats on top of the water and does not effect % transmittance. Silicone surfactants such as Union Carbide Silwet L77 and Silwet L7605 exhibit inverse cloud point phenomena, making the water milky above the inverse cloud point and dramatically lower the % transmittance over that temperature. These materials do not however become particulate, hence the % transmission remains low. Traditional commercial nonionics such as blocked polymers like Alkatronic PGP-18-1 and ethoxylated alkyl phenols like nonoxynol 9 are similar to the silicone surfactants in that emulsions foam at inverse cloud point which makes the solution milky, and decreases % transmittance. These materials cease to foam themselves but do not as effectively defoam as do particulates like ethylene-bis-stearamide and compounds of the present invention. The subject of this invention demonstrated by alkoxylated bis-amides example 2 becomes milky only briefly, then becomes insoluble and particulate in water, floats to the top where its antifoaming action occurs and is effectively removed from solution preventing any effect upon % transmittance. This alkoxylated bis-amide enjoys the positive effect of ethylene-bis-stearamide, insolubility, yet below its inverse cloud point has the advantage of solubility which ethylene-bis-stearamide does not exhibit.

The defoamer compositions of this invention are also useful in the reduction of existing foam (knockdown) and prevention of foam formation (hold-down) which occurs, for example, in brown stock washer liquor during the pulping process. When used for this purpose, from about 0.003 to about 0.5 parts by weight of defoamer solids are added to the pulp, per 100 parts by weight of dry pulp.

Additionally, this compounds of this invention continue to defoam upon repeated agitation. Ethylene-bis-stearamide shows decrease in effectiveness upon re-testing. To demonstrate this formulations A,B,C and D in Table III were tested by the cylinder shake foam test, then allowed to stand five minutes and then reshaken. This allowed for the evaluation of the effectiveness of the defoamer formulation after repeated challenge as would be the case in a commercial process.

TABLE I
CYLINDER SHAKE FOAM TEST FORMULATIONS
% by weight

| Formula | A | B | C | D |
|---|---|---|---|---|
| Ethylene-bis-stearmide | 5.0 | 0.0 | 0.0 | 2.5 |
| Acryloid polymer | | | 2.0 | |
| Silicone oil | | | 1.0 | |
| Mineral oil | | | QS | |
| Compound Example #56 | 0.0 | 5.0 | 0.0 | 2.5 |
| Compound Example #83 | 0.0 | 0.0 | 5.0 | 0.0 |
| Hydrophoic Silica | 0.0 | 0.0 | 0.0 | 2.5 |
| Total | | | 100.00% by weight | |

Cylinder shake foam test results conducted with formulas A,B,C, and D are as follows;

Formula A is the standard formulation against which all others are measured.

Formula B is better initially in defoaming properties and is much more effective after 5 retests.

Formula C is slightly less effective than Formulation B, but is better than Formulation A.

Formula D has hydrophobic silica added to the formulation. This increases initial knock down, but after 5 retests looses effectiveness. These tests demonstrate that the compositions of this invention are effective defoamers compared to existing commercial defoamers. The apparatus and method described above may also be used to evaluate the defoamer composition in any liquid which forms foam during agitation and/or heating. Other aqueous systems which may be defoamed with these invert defoamer compositions include kraft screen room bleach plant applications, pulp and paper mill effluents, animal glues, other adhesives, latex, starches, other resinous systems, water base paints and the like.

| Examples | Raw Material Examples |
|---|---|
| Reactant A | Alcohol Alkoxylate |

Alkoxylated alcohols are known to those skilled in the art and are available from many commercial sources, including Shell Chemical and Vista Chemical. The examples given here are illustrative of the preferred species of the current invention.

Compounds useful as raw materials in the preparation of the compounds of this invention conform to the following generic structure;

$$R-O-(CH_2CH_2O)_x(CH_2CHO)_y(CH_2CH_2O)_z-H$$
$$|$$
$$CH_3$$

| Example # | x | y | z | Alcohol ($R^3$) |
|---|---|---|---|---|
| Raw Material Example #1 | 0 | 2 | 5 | C20H41 |
| Raw Material Example #2 | 5 | 5 | 5 | C20H41 |
| Raw Material Example #3 | 10 | 10 | 10 | C20H41 |
| Raw Material Example #4 | 0 | 2 | 5 | C18H37 |
| Raw Material Example #5 | 5 | 5 | 5 | C18H37 |
| Raw Material Example #6 | 10 | 10 | 10 | C18H37 |
| Raw Material Example #7 | 0 | 10 | 0 | C18H37 |
| Raw Material Example #8 | 0 | 0 | 2 | C18H37 |
| Raw Material Example #9 | 0 | 2 | 5 | C16H33 |
| Raw Material Example #10 | 5 | 5 | 5 | C16H33 |
| Raw Material Example #11 | 10 | 10 | 10 | C16H33 |
| Raw Material Example #12 | 0 | 10 | 0 | C16H33 |
| Raw Material Example #13 | 0 | 0 | 2 | C16H33 |
| Raw Material Example #14 | 0 | 2 | 5 | C14H29 |
| Raw Material Example #15 | 5 | 5 | 5 | C14H29 |
| Raw Material Example #16 | 10 | 10 | 10 | C14H29 |
| Raw Material Example #17 | 0 | 2 | 5 | C12H25 |
| Raw Material Example #18 | 5 | 5 | 5 | C12H25 |
| Raw Material Example #19 | 10 | 10 | 10 | C12H25 |

Reactant B
Acid Source

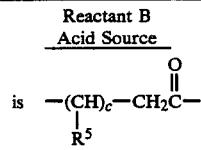

| Acid Source | c | $R^5$ |
|---|---|---|
| Acrylic Acid | 2 | H |
| Methacrylic acid | 2 | $CH_3$ |
| Butryolactone | 3 | H |
| Chloracetic | 1 | H |

$$R^3-O-(CH_2CH_2O)_x(CH_2CHO)_y(CH_2CH_2O)_z-(CH_2)_2C(O)OH$$
$$|$$
$$CH_3$$

EXAMPLE 1

To a suitable reaction vessel is added 619.0 grams of Raw Material Example #1, which has been stripped of moisture. 200 ppm hydroquinone monomethylether and 72 grams of acrylic acid is then added at between 40°–50° C., while sparging with air. The reaction mass is then heated to 80°–100° C. for 3 to 5 hours. The product is obtained in 97% purity, and conforms to the following structure;

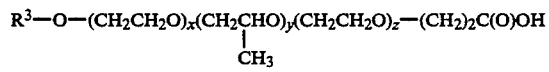

R³ is C20H41 x is 0 y is 2 z is 5.

EXAMPLE 2

To a suitable reaction vessel is added 1016.0 grams of Raw Material Example #2, which has been stripped of moisture. 200 ppm hydroquinone monomethylether and 72 grams of acrylic acid is then added at between 40°-50° C., while sparging with air. The reaction mass is then heated to 80°-100° C. for 3 to 5 hours. The product is obtained in 97% purity, and conforms to the following structure;

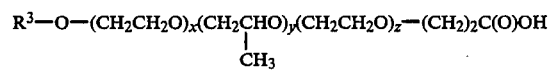

R³ is C20H41 x is 5 y is 5 z is 5.

EXAMPLE 3

To a suitable reaction vessel is added 1751.0 grams of Raw Material Example #3, which has been stripped of moisture. 200 ppm hydroquinone monomethylether and 72 grams of acrylic acid is then added at between 40°-50° C., while sparging with air. The reaction mass is then heated to 80°-100° C. for 3 to 5 hours. The product is obtained in 97% purity, and conforms to the following structure;

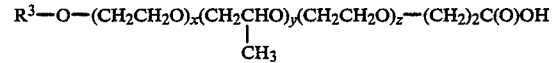

R³ is C20H41 x is 10 y is 10 z is 10.

EXAMPLE 4

To a suitable reaction vessel is added 591.0 grams of Raw Material Example #4, which has been stripped of moisture. 200 ppm hydroquinone monomethylether and 72 grams of acrylic acid is then added at between 40°-50° C., while sparging with air. The reaction mass is then heated to 80°-100° C., for 3 to 5 hours. The product is obtained in 97% purity, and conforms to the following structure;

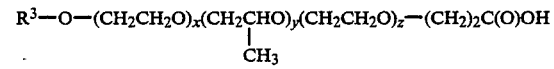

R³ is C18H37 x is 0 y is 2 z is 5.

EXAMPLE 5

To a suitable reaction vessel is added 988.0 grams of Raw Material Example #5, which has been stripped of moisture. 200 ppm hydroquinone monomethylether and 72 grams of acrylic acid is then added at between 40°-50° C., while sparging with air. The reaction mass is then heated to 80°-100° C., for 3 to 5 hours. The product is obtained in 97% purity, and conforms to the following structure;

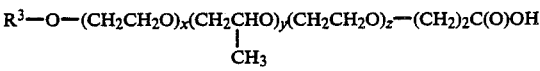

R³ is C18H37 x is 5 y is 5 z is 5.

EXAMPLE 6

To a suitable reaction vessel is added 1723.0 grams of Raw Material Example #6, which has been stripped of moisture. 200 ppm hydroquinone monomethylether and 72 grams of acrylic acid is then added at between 40°-50° C., while sparging with air. The reaction mass is then heated to 80°-100° C., for 3 to 5 hours. The product is obtained in 97% purity, and conforms to the following structure;

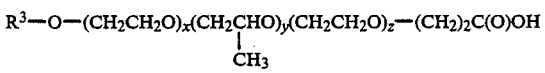

R³ is C18H37 x is 10 y is 10 z is 10.

EXAMPLE 7

To a suitable reaction vessel is added 843.0 grams of Raw Material Example #7, which has been stripped of moisture. 200 ppm hydroquinone monomethylether and 72 grams of acrylic acid is then added at between 40°-50° C., while sparging with air. The reaction mass is then heated to 80°-100° C., for 3 to 5 hours. The product is obtained in 97% purity, and conforms to the following structure;

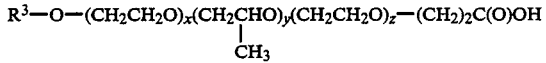

R³ is C18H37 x is 0 y is 10 z is 0.

EXAMPLE 8

To a suitable reaction vessel is added 341.0 grams of Raw Material Example #8, which has been stripped of moisture. 200 ppm hydroquinone monomethylether and 72 grams of acrylic acid is then added at between 40°-50° C., while sparging with air. The reaction mass is then heated to 80°-100° C., for 3 to 5 hours. The product is obtained in 97% purity, and conforms to the following structure;

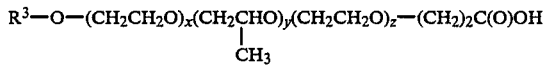

R³ is C18H37 x is 0 y is p0 z is 2.

EXAMPLE 9

To a suitable reaction vessel is added 313.0 grams of Raw Material Example #9, which has been stripped of moisture. 200 ppm hydroquinone monomethylether and 72 grams of acrylic acid is then added at between 40°-50° C., while sparging with air. The reaction mass is then heated to 80°-100° C., for 3 to 5 hours. The product is obtained in 97% purity, and conforms to the following structure;

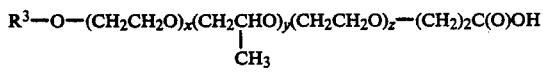

R³ is C16H33 x is 0 y is 2 z is 5.

EXAMPLE 10

To a suitable reaction vessel is added 842.0 grams of Raw Material Example #10, which has been stripped of moisture. 200 ppm hydroquinone monomethylether and 72 grams of acrylic acid is then added at between 40°–50° C., while sparging with air. The reaction mass is then heated to 80°–100° C., for 3 to 5 hours. The product is obtained in 97% purity, and conforms to the following structure;

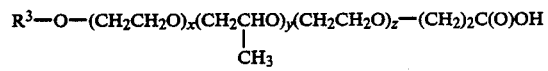

R³ is C16H33 x is 5 y is 5 z is 5.

EXAMPLE 11

To a suitable reaction vessel is added 1695.0 grams of Raw Material Example #11, which has been stripped of moisture. 200 ppm hydroquinone monomethylether and 72 grams of acrylic acid is then added at between 40°–50° C., while sparging with air. The reaction mass is then heated to 80°–100° C., for 3 to 5 hours. The product is obtained in 97% purity, and conforms to the following structure;

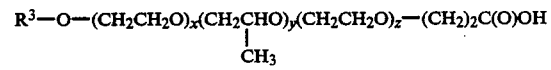

R³ is C16H33 x is 10 y is 10 z is 10.

EXAMPLE 12

To a suitable reaction vessel is added 815.0 grams of Raw Material Example #12, which has been stripped of moisture. 200 ppm hydroquinone monomethylether and 72 grams of acrylic acid is then added at between 40°–50° C., while sparging with air. The reaction mass is then heated to 80°–100° C., for 3 to 5 hours. The product is obtained in 97% purity, and conforms to the following structure;

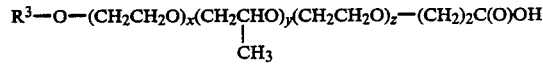

R³ is C16H33 x is 0 y is 10 z is 0.

EXAMPLE 13

To a suitable reaction vessel is added 313.0 grams of Raw Material Example #13, which has been stripped of moisture. 200 ppm hydroquinone monomethylether and 72 grams of acrylic acid is then added at between 40°–50° C., while sparging with air. The reaction mass is then heated to 80°–100° C., for 3 to 5 hours. The product is obtained in 97% purity, and conforms to the following structure;

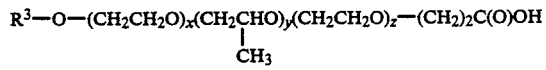

R³ is C16H33 x is 0 y is 0 z is 2.

EXAMPLE 14

To a suitable reaction vessel is added 535.0 grams of Raw Material Example #14, which has been stripped of moisture. 200 ppm hydroquinone monomethylether and 72 grams of acrylic acid is then added at between 40°–50° C., while sparging with air. The reaction mass is then heated to 80°–100° C., for 3 to 5 hours. The product is obtained in 97% purity, and conforms to the following structure;

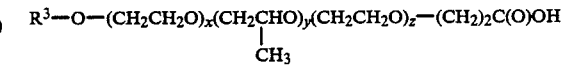

R³ is C14H229 x is 0 y is 2 z is 5.

EXAMPLE 15

To a suitable reaction vessel is added 932.0 grams of Raw Material Example #15, which has been stripped of moisture. 200 ppm hydroquinone monomethylether and 72 grams of acrylic acid is then added at between 40°–50° C., while sparging with air. The reaction mass is then heated to 80°–100° C., for 3 to 5 hours. The product is obtained in 97% purity, and conforms to the following structure;

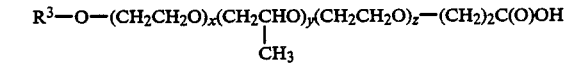

R³ is C14H29 x is 5 y is 5 z is 5.

EXAMPLE 16

To a suitable reaction vessel is added 1667.0 grams of Raw Material Example #16, which has been stripped of moisture. 200 ppm hydroquinone monomethylether and 72 grams of acrylic acid is then added at between 40°–50° C., while sparging with air. The reaction mass is then heated to 80°–100° C., for 3 to 5 hours. The product is obtained in 97% purity, and conforms to the following structure;

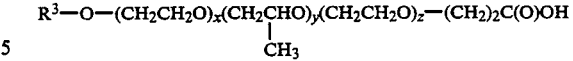

R³ is C14H29 x is 10 y is 10 z is 10.

EXAMPLE 17

To a suitable reaction vessel is added 507.0 grams of Raw Material Example #17, which has been stripped of moisture. 200 ppm hydroquinone monomethylether and 72 grams of acrylic acid is then added at between 40°–50° C., while sparging with air. The reaction mass is then heated to 80°–100° C., for 3 to 5 hours. The product is obtained in 97% purity, and conforms to the following structure;

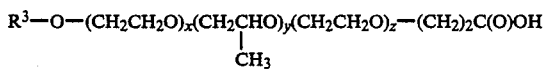

R³ is C12H25 x is 0 y is 2 z is 5.

EXAMPLE 18

To a suitable reaction vessel is added 904.0 grams of Raw Material Example #19, which has been stripped of moisture. 200 ppm hydroquinone monomethylether and 72 grams of acrylic acid is then added at between 40°–50° C., while sparging with air. The reaction mass is then heated to 80°–100° C., for 3 to 5 hours. The product is obtained in 97% purity, and conforms to the following structure;

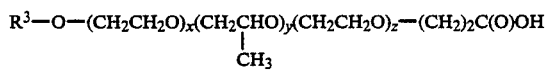

R³ is C12H25 x is 5 y is 5 z is 5.

EXAMPLE 19

To a suitable reaction vessel is added 1639.0 grams of Raw Material Example #19, which has been stripped of moisture. 200 ppm hydroquinone monomethylether and 72 grams of acrylic acid is then added at between 40°–50° C., while sparging with air. The reaction mass is then heated to 80°–100° C., for 3 to 5 hours. The product is obtained in 97% purity, and conforms to the following structure;

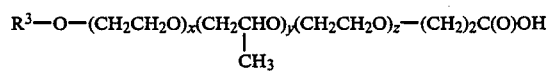

R³ is C12H25 x is 10 y is 10 z is 10.

EXAMPLE 20

Repeat Example 1 only this time replacing the 72.0 grams of acrylic acid with 86.0 grams of methacrylic acid.

EXAMPLE 21

Repeat Example 2 only this time replacing the 72.0 grams of acrylic acid with 86.0 grams of methacrylic acid.

EXAMPLE 22

Repeat Example 3 only this time replacing the 72.0 grams of acrylic acid with 86.0 grams of methacrylic acid.

EXAMPLE 23

Repeat Example 4 only this time replacing the 72.0 grams of acrylic acid with 86.0 grams of methacrylic acid.

EXAMPLE 24

Repeat Example 5 only this time replacing the 72.0 grams of acrylic acid with 86.0 grams of methacrylic acid.

EXAMPLE 25

Repeat Example 6 only this time replacing the 72.0 grams of acrylic acid with 86.0 grams of methacrylic acid.

EXAMPLE 26

Repeat Example 7 only this time replacing the 72.0 grams of acrylic acid with 86.0 grams of methacrylic acid.

EXAMPLE 27

Repeat Example 8 only this time replacing the 72.0 grams of acrylic acid with 86.0 grams of methacrylic acid.

EXAMPLE 28

Repeat Example 9 only this time replacing the 72.0 grams of acrylic acid with 86.0 grams of methacrylic acid.

EXAMPLE 29

Repeat Example 10 only this time replacing the 72.0 grams of acrylic acid with 86.0 grams of methacrylic acid.

EXAMPLE 30

Repeat Example 11 only this time replacing the 72.0 grams of acrylic acid with 86.0 grams of methacrylic acid.

EXAMPLE 31

Repeat Example 12 only this time replacing the 72.0 grams of acrylic acid with 86.0 grams of methacrylic acid.

EXAMPLE 32

Repeat Example 13 only this time replacing the 72.0 grams of acrylic acid with 86.0 grams of methacrylic acid.

EXAMPLE 33

Repeat Example 14 only this time replacing the 72.0 grams of acrylic acid with 86.0 grams of methacrylic acid.

EXAMPLE 34

Repeat Example 15 only this time replacing the 72.0 grams of acrylic acid with 86.0 grams of methacrylic acid.

EXAMPLE 35

Repeat Example 16 only this time replacing the 72.0 grams of acrylic acid with 86.0 grams of methacrylic acid.

EXAMPLE 36

Repeat Example 17 only this time replacing the 72.0 grams of acrylic acid with 86.0 grams of methacrylic acid.

EXAMPLE 37

Repeat Example 18 only this time replacing the 72.0 grams of acrylic acid with 86.0 grams of methacrylic acid.

EXAMPLE 38

Repeat Example 19 only this time replacing the 72.0 grams of acrylic acid with 86.0 grams of methacrylic acid.

EXAMPLE 39

To a suitable reaction vessel is added 619.0 grams of Raw Material Example #1. Next, 56.1 grams of potassium hydroxide is added. The reaction mass is then heated to 100°-200° C. Then, 86.0 grams of n-butyrolactone is added. Reaction temperature is held between 100° and 120° C. for four to six hours. The reaction mass is cooled to ambient temperature and washed with dilute aqueous hydrochloric acid to remove potassium chloride. The aqueous layer is discarded. Subsequently, the organic phase is washed two times and the pH is 3-4. The product is obtained in 97% purity, and conforms to the following structure;

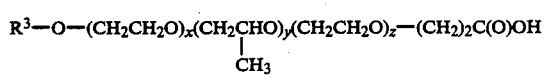

$R^3$ is C20H41 x is 0 y is 2 z is 5.

EXAMPLE 40

To a suitable reaction vessel is added 1016.0 grams of Raw Material Example #2. Next, 56.1 grams of potassium hydroxide is added. The reaction mass is then heated to 100°-120° C. Then, 86.0 grams of n-butyrolactone is added. Reaction temperature is held between 100° and 120° C., for four to six hours. The reaction mass is cooled to ambient temperature and washed with dilute aqueous hydrochloric acid to remove potassium chloride. The aqueous layer is discarded. Subsequently, the organic phase is washed two times and the pH is 3-4. The product is obtained in 97% purity, and conforms to the following structure;

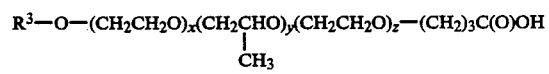

$R^3$ is C20H41 x is 5 y is 5 z is 5.

EXAMPLE 41

To a suitable reaction vessel is added 1751.0 grams of Raw Material Example #3. Next, 56.1 grams of potassium hydroxide is added. The reaction mass is then heated to 100°-120° C. Then, 86.0 grams of n-butyrolactone is added. Reaction temperature is held between 100° and 120° C., for four to six hours. The reaction mass is cooled to ambient temperature and washed with dilute aqueous hydrochloric acid to remove potassium chloride. The aqueous layer is discarded. Subsequently, the organic phase is washed two times and the pH is 3-4. The product is obtained in 97% purity, and conforms to the following structure;

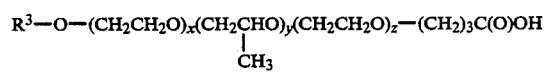

$R^3$ is C20H41 x is 10 y is 10 z is 10.

EXAMPLE 42

To a suitable reaction vessel is added 591.0 grams of Raw Material Example #4. Next, 56.1 grams of potassium hydroxide is added. The reaction mass is then heated to 100°-120° C. Then, 86.0 grams of n-butyrolactone is added. Reaction temperature is held between 100° and 120° C., for four to six hours. The reaction mass is cooled to ambient temperature and washed with dilute aqueous hydrochloric acid to remove potassium chloride. The aqueous layer is discarded. Subsequently, the organic phase is washed two times and the pH is 3-4. The product is obtained in 97% purity, and conforms to the following structure;

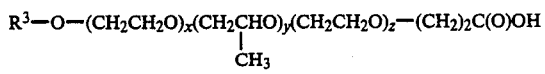

$R^3$ is C18H37 x is 0 y is 2 z is 5.

EXAMPLE 43

To a suitable reaction vessel is added 988.0 grams of Raw Material Example #5. Next, 56.1 grams of potassium hydroxide is added. The reaction mass is then heated to 100°-120° C. Then, 86.0 grams of n-butyrolactone is added. Reaction temperature is held between 100° and 120° C., for four to six hours. The reaction mass is cooled to ambient temperature and washed with dilute aqueous hydrochloric acid to remove potassium chloride. The aqueous layer is discarded. Subsequently, the organic phase is washed two times and the pH is 3-4. The product is obtained in 97% purity, and conforms to the following structure;

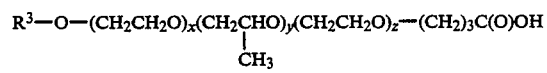

$R^3$ is C18H37 x is 5 y is 5 z is 5.

EXAMPLE 44

To a suitable reaction vessel is added 17223.0 grams of Raw Material Example #6. Next, 56.1 grams of potassium hydroxide is added. The reaction mass is then heated to 100°-120° C. Then, 86.0 grams of n-butyrolactone is added. Reaction temperature is held between 100° and 120° C., for four to six hours. The reaction mass is cooled to ambient temperature and washed with dilute aqueous hydrochloric acid to remove potassium chloride. The aqueous layer is discarded. Subsequently, the organic phase is washed two times and the pH is 3-4. The product is obtained in 97% purity, and conforms to the following structure;

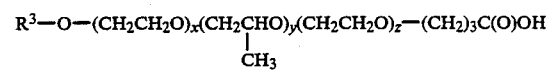

$R^3$ is C18H37 x is 10 y is 10 z is 10.

EXAMPLE 45

To a suitable reaction vessel is added 843.0 grams of Raw Material Example #7. Next, 56.1 grams of potassium hydroxide is added. The reaction mass is then heated to 100°-120° C. Then, 86.0 grams of n-butyrolactone is added. Reaction temperature is held between 100° and 120° C., for four to six hours. The reaction mass is cooled to ambient temperature and washed with dilute aqueous hydrochloric acid to remove potassium chloride. The aqueous layer is discarded. Subsequently, the organic phase is washed two times and the pH is 3-4. The product is obtained in 97% purity, and conforms to the following structure;

$$R^3-O-(CH_2CH_2O)_x(CH_2CHO)_y(CH_2CH_2O)_z-(CH_2)_3C(O)OH$$
$$|$$
$$CH_3$$

$R^3$ is C18H37 x is 0 y is 10 z is 0.

EXAMPLE 46

Repeat Example 39 only this time replacing the butyrolactone with 116.5 grams of sodium monochloracete.

EXAMPLE 47

Repeat Example 40 only this time replacing the butyrolactone with 116.5 grams of sodium monochloracete.

EXAMPLE 48

Repeat Example 41 only this time replacing the butyrolactone with 116.5 grams of sodium monochloracete.

EXAMPLE 49

Repeat Example 43 only this time replacing the butyrolactone with 116.5 grams of sodium monochloracete.

EXAMPLE 50

Repeat Example 45 only this time replacing the butyrolactone with 116.5 grams of sodium monochloracete.

EXAMPLES 51–99

To the specified amount of the specified example (1 to 50) is added the specified amount of the specified diamine. The reaction mass is heated to 180°–190° C. and held for 5 to 10 hours. Water begins to distill off at about 140° C., indicating the formation of the desired amide. The reaction is complete when the free amine and free carboxylic acid level become vanishing small. The product is used as is without additional work up.

| Example # | Ethylene diamine Grams | Alkoxy Ester Example | Grams Alkoxy ester |
|---|---|---|---|
| 51 | 60.0 grams | Example #1 | 691.0 |
| 52 | 60.0 grams | Example #2 | 1088.0 |
| 53 | 60.0 grams | Example #3 | 1823.0 |
| 54 | 60.0 grams | Example #4 | 663.0 |
| 55 | 60.0 grams | Example #5 | 1060.0 |
| 56 | 60.0 grams | Example #6 | 1795.0 |
| 57 | 60.0 grams | Example #7 | 915.0 |
| 58 | 60.0 grams | Example #8 | 413.0 |
| 59 | 60.0 grams | Example #9 | 384.0 |
| 60 | 60.0 grams | Example #10 | 914.0 |
| 61 | 60.0 grams | Example #11 | 1767.0 |
| 62 | 60.0 grams | Example #12 | 887.0 |
| 63 | 60.0 grams | Example #13 | 385.0 |
| 64 | 60.0 grams | Example #14 | 607.0 |
| 65 | 60.0 grams | Example #15 | 1004.0 |
| 66 | 60.0 grams | Example #16 | 1739.0 |
| 67 | 60.0 grams | Example #17 | 579.0 |
| 68 | 60.0 grams | Example #18 | 976.0 |
| 69 | 60.0 grams | Example #19 | 1711.0 |
| 70 | 60.0 grams | Example #20 | 706.0 |
| 71 | 60.0 grams | Example #21 | 1103.0 |
| 72 | 60.0 grams | Example #22 | 1838.0 |
| 73 | 60.0 grams | Example #23 | 678.0 |
| 74 | 60.0 grams | Example #24 | 1075.0 |
| 75 | 60.0 grams | Example #25 | 1810.0 |
| 76 | 60.0 grams | Example #26 | 930.0 |
| 77 | 60.0 grams | Example #27 | 928.0 |
| 78 | 60.0 grams | Example #28 | 400.0 |
| 79 | 60.0 grams | Example #29 | 929.0 |
| 80 | 60.0 grams | Example #30 | 1782.0 |
| 81 | 60.0 grams | Example #31 | 902.0 |
| 82 | 60.0 grams | Example #32 | 400.0 |
| 83 | 60.0 grams | Example #33 | 622.0 |
| 84 | 60.0 grams | Example #34 | 1019.0 |
| 85 | 60.0 grams | Example #35 | 1754.0 |
| 86 | 60.0 grams | Example #36 | 594.0 |
| 87 | 60.0 grams | Example #37 | 991.0 |
| 88 | 60.0 grams | Example #38 | 1726.0 |
| 89 | 60.0 grams | Example #39 | 706.0 |
| 90 | 60.0 grams | Example #40 | 1103.0 |
| 91 | 60.0 grams | Example #41 | 1838.0 |
| 92 | 60.0 grams | Example #42 | 678.0 |
| 93 | 60.0 grams | Example #43 | 1075.0 |
| 94 | 60.0 grams | Example #44 | 1810.0 |
| 95 | 60.0 grams | Example #45 | 930.0 |
| 96 | 60.0 grams | Example #46 | 678.0 |
| 97 | 60.0 grams | Example #47 | 1075.0 |
| 98 | 60.0 grams | Example #48 | 1810.0 |
| 99 | 60.0 grams | Example #49 | 650.0 |
| 100 | 60.0 grams | Example #50 | 1047.0 |

What is claimed:

1. A defoaming composition containing an effective defoaming amount of a defoamer which conforms to the following structure;

$$R^1-N-R^2-N-R^1$$
$$|\phantom{-N-R^2-N-}|$$
$$H\phantom{-N-R^2-N-}H$$

wherein;
$R^1$ is $$R^3-O-(CH_2CH_2O)_x(CH_2CHO)_y(CH_2CH_2O)_z-R^4-;$$
$$|$$
$$CH_3$$

$R^2$ is $-(CH_2)_a-$;
$R^3$ is alkyl $C_{12}$ to $C_{20}$;

$$R^4 \text{ is } -(CH)_c-CH_2\overset{O}{\overset{\|}{C}}-;$$
$$\phantom{R^4 \text{ is } -}|$$
$$\phantom{R^4 \text{ is } -}R^5$$

x,y,z are each independently integers from 0 to 20;
a is an integer from 1 to 5;
c is an integer from 0 to 5;
$R^5$ is selected from H, $CH_3$, $C_2H_5$, $C_3H_6$.

2. A composition as claimed in claim 1 wherein;
$R^2$ is $-(CH_2)_2-$.

3. A composition as claimed in claim 1 wherein;

$$R^4 \text{ is } -CH_2-CH_2-\overset{O}{\overset{\|}{C}}-.$$

4. A composition as claimed in claim 1 wherein;

$$R^4 \text{ is } -(CH)-CH_2\overset{O}{\overset{\|}{C}}-.$$
$$\phantom{R^4 \text{ is } -}|$$
$$\phantom{R^4 \text{ is } -}CH_3$$

5. A composition as claimed in claim 1 wherein;

$R^4$ is $-CH_2CH_2CH_2\overset{\overset{O}{\|}}{C}-$.

6. A composition as claimed in claim 1 wherein;

$R^4$ is $-CH_2\overset{\overset{O}{\|}}{C}-$.

7. A composition as claimed in claim 1 additionally including a member selected from the group consisting of mineral oil, silicone oil, hydrophobic silica, ethylene-bis-stearamide, or a guerbet alcohol.

8. A compound conforming to the following structure;

$$R^1-\underset{H}{N}-R^2-\underset{H}{N}-R^1$$

Wherein;
$R^1$ is $$R^3-O-(CH_2CH_2O)_x(CH_2\underset{CH_3}{C}HO)_y(CH_2CH_2O)_x-R^4-$$

$R^2$ is $-(CH_2)_a-$
$R^3$ is alkyl $C_{12}$ to $C_{20}$;

$R^4$ is $-(CH)_c-CH_2\overset{\overset{O}{\|}}{C}-$;
      $\quad\quad\ \ |$
      $\quad\quad\ \ R^5$ x,y,z are each independently integers from 0 to 20;
a is an integer from 1 to 5;
c is an integer from 0 to 5;
$R^5$ is selected from H, $CH_3$, $C_2H_5$, $C_3H_6$.

9. A compound as claimed in claim 8 wherein;
$R^2$ is $-(CH_2)_2-$.

10. A compound as claimed in claim 8 wherein;

$R^4$ is $-CH_2-CH_2\overset{\overset{O}{\|}}{C}-$.

11. A compound as claimed in claim 8 wherein;

$R^4$ is $-(CH)-CH_2\overset{\overset{O}{\|}}{C}-$.
      $\quad\ \ |$
      $\quad\ \ CH_3$ 12. A compound as claimed in claim 8 wherein;

$R^4$ is $-CH_2CH_2CH_2\overset{\overset{O}{\|}}{C}-$.

13. A compound as claimed in claim 8 wherein;

$R^4$ is $-CH_2\overset{\overset{O}{\|}}{C}-$.

* * * * *